(12) United States Patent
Brown

(10) Patent No.: US 9,314,303 B2
(45) Date of Patent: Apr. 19, 2016

(54) LASER SURGERY CONTROLLER WITH VARIABLE TIME DELAY AND FEEDBACK DETECTOR SENSITIVITY CONTROL

(76) Inventor: Joe Denton Brown, Panama City Beach, FL (US)

( * ) Notice: Subject to any disclaimer, the term of this patent is extended or adjusted under 35 U.S.C. 154(b) by 0 days.

(21) Appl. No.: 13/070,247

(22) Filed: Mar. 23, 2011

(65) Prior Publication Data

US 2011/0238048 A1 Sep. 29, 2011

Related U.S. Application Data

(60) Provisional application No. 61/316,569, filed on Mar. 23, 2010.

(51) Int. Cl.
*A61B 18/22* (2006.01)
*A61B 17/00* (2006.01)
*A61B 18/00* (2006.01)

(52) U.S. Cl.
CPC ....... *A61B 18/22* (2013.01); *A61B 2017/00084* (2013.01); *A61B 2018/00642* (2013.01)

(58) Field of Classification Search
CPC ................. A61B 18/20; A61B 18/22; A61B 2017/00084; A61B 2018/00642; A61B 2018/202; A61N 2005/0626; A61N 2005/0627; A61N 2005/063; A61F 2009/00844
USPC ...................................................... 607/88–94
See application file for complete search history.

(56) References Cited

U.S. PATENT DOCUMENTS

| | | |
|---|---|---|
| 3,912,362 A | 10/1975 | Hudson |
| 4,060,308 A | 11/1977 | Barnoski et al. |
| 4,385,832 A | 5/1983 | Doi et al. |
| 4,474,429 A | 10/1984 | Yoldas et al. |
| 4,519,390 A | 5/1985 | Horne |
| 4,543,477 A | 9/1985 | Doi et al. |
| 4,575,181 A | 3/1986 | Ishikawa |
| 4,669,465 A | 6/1987 | Moore et al. |
| 4,678,273 A | 7/1987 | Vilhelmsson |
| 4,718,417 A | 1/1988 | Kittrell et al. |
| 4,737,011 A | 4/1988 | Iri et al. |
| 4,760,845 A | 8/1988 | Kovalcheck |
| 4,762,385 A | 8/1988 | Fuse |
| 4,784,466 A | 11/1988 | Khoe et al. |
| 4,832,024 A | 5/1989 | Boussignac et al. |
| 4,883,054 A | 11/1989 | Fuller et al. |
| 4,883,342 A | 11/1989 | Ishii et al. |
| 4,913,142 A | 4/1990 | Kittrell et al. |
| 4,994,059 A | 2/1991 | Kosa et al. |
| 5,057,099 A | 10/1991 | Rink |
| 5,061,265 A | 10/1991 | Abela et al. |
| 5,098,427 A | 3/1992 | Hessel et al. |
| 5,101,457 A | 3/1992 | Blonder et al. |
| 5,132,079 A | 7/1992 | Stewart et al. |
| 5,154,707 A | 10/1992 | Rink et al. |
| 5,179,610 A | 1/1993 | Milburn et al. |
| 5,188,632 A * | 2/1993 | Goldenberg ..................... 606/7 |
| 5,196,005 A | 3/1993 | Doiron et al. |
| 5,219,345 A | 6/1993 | Potter |
| 5,243,681 A | 9/1993 | Bowen et al. |

(Continued)

*Primary Examiner* — Lynsey Crandall
*Assistant Examiner* — Nathan J Jenness
(74) *Attorney, Agent, or Firm* — Bacon & Thomas, PLLC

(57) ABSTRACT

A handheld controller for laser surgical applications includes a variable time delay control to allow a surgeon to delay interruption of laser firing in response to feedback from an overheating detector, and a detector sensitivity control for changing a sensitivity of the detector.

9 Claims, 1 Drawing Sheet

(56) References Cited

U.S. PATENT DOCUMENTS

| | | | |
|---|---|---|---|
| 5,274,721 A | 12/1993 | Dickinson et al. | |
| 5,291,570 A | 3/1994 | Filgas et al. | |
| 5,299,141 A | 3/1994 | Hungerford et al. | |
| 5,300,066 A | 4/1994 | Manoukian et al. | |
| 5,330,465 A | 7/1994 | Doiron et al. | |
| 5,354,323 A | 10/1994 | Whitebook | |
| 5,490,227 A | 2/1996 | Tanabe et al. | |
| 5,569,240 A | 10/1996 | Dowlatshahi et al. | |
| 5,619,602 A | 4/1997 | Sandrstom et al. | |
| 5,649,923 A | 7/1997 | Gregory et al. | |
| 5,820,627 A | 10/1998 | Rosen et al. | |
| 5,829,445 A | 11/1998 | Martin et al. | |
| 5,928,222 A | 7/1999 | Kleinerman | |
| 5,946,437 A | 8/1999 | Uchida et al. | |
| 5,968,033 A | 10/1999 | Fuller et al. | |
| 6,015,404 A * | 1/2000 | Altshuler et al. | 606/9 |
| 6,154,596 A | 11/2000 | Ionov | |
| 6,282,349 B1 | 8/2001 | Griffin | |
| 6,345,215 B1 * | 2/2002 | Drechsler | 700/306 |
| 6,389,307 B1 | 5/2002 | Abela | |
| 6,398,777 B1 | 6/2002 | Navarro et al. | |
| 7,204,645 B2 | 4/2007 | Brown | |
| 2002/0045811 A1 | 4/2002 | Kittrell et al. | |
| 2002/0068963 A1 | 6/2002 | Maki et al. | |
| 2003/0023236 A1 | 1/2003 | Gowda et al. | |
| 2004/0006333 A1 | 1/2004 | Arnold et al. | |
| 2004/0092913 A1 | 5/2004 | Hennings et al. | |
| 2004/0147912 A1 | 7/2004 | Sinofsky | |
| 2004/0147913 A1 | 7/2004 | Sinofsky | |
| 2004/0162490 A1 | 8/2004 | Soltz et al. | |
| 2004/0249261 A1 | 12/2004 | Torchia et al. | |
| 2005/0038419 A9 | 2/2005 | Arnold et al. | |
| 2005/0107852 A1 * | 5/2005 | Levernier et al. | 607/89 |
| 2005/0124985 A1 | 6/2005 | Takayama et al. | |
| 2005/0131400 A1 | 6/2005 | Hennings et al. | |
| 2005/0267452 A1 | 12/2005 | Farr et al. | |
| 2005/0273090 A1 | 12/2005 | Nieman et al. | |
| 2005/0288654 A1 | 12/2005 | Nieman et al. | |
| 2005/0288655 A1 | 12/2005 | Root et al. | |
| 2006/0052661 A1 | 3/2006 | Gannot et al. | |
| 2006/0122587 A1 | 6/2006 | Sharareh | |
| 2006/0217692 A1 | 9/2006 | Neuberger | |
| 2006/0217693 A1 | 9/2006 | Gowda et al. | |
| 2006/0253178 A1 | 11/2006 | Masotti | |
| 2008/0058783 A1 * | 3/2008 | Altshuler et al. | 606/9 |
| 2009/0062782 A1 | 3/2009 | Brown | |
| 2009/0112199 A1 * | 4/2009 | Zhang et al. | 606/15 |
| 2009/0149845 A1 | 6/2009 | Brown | |
| 2009/0299353 A1 * | 12/2009 | Lewinsky et al. | 606/16 |

* cited by examiner

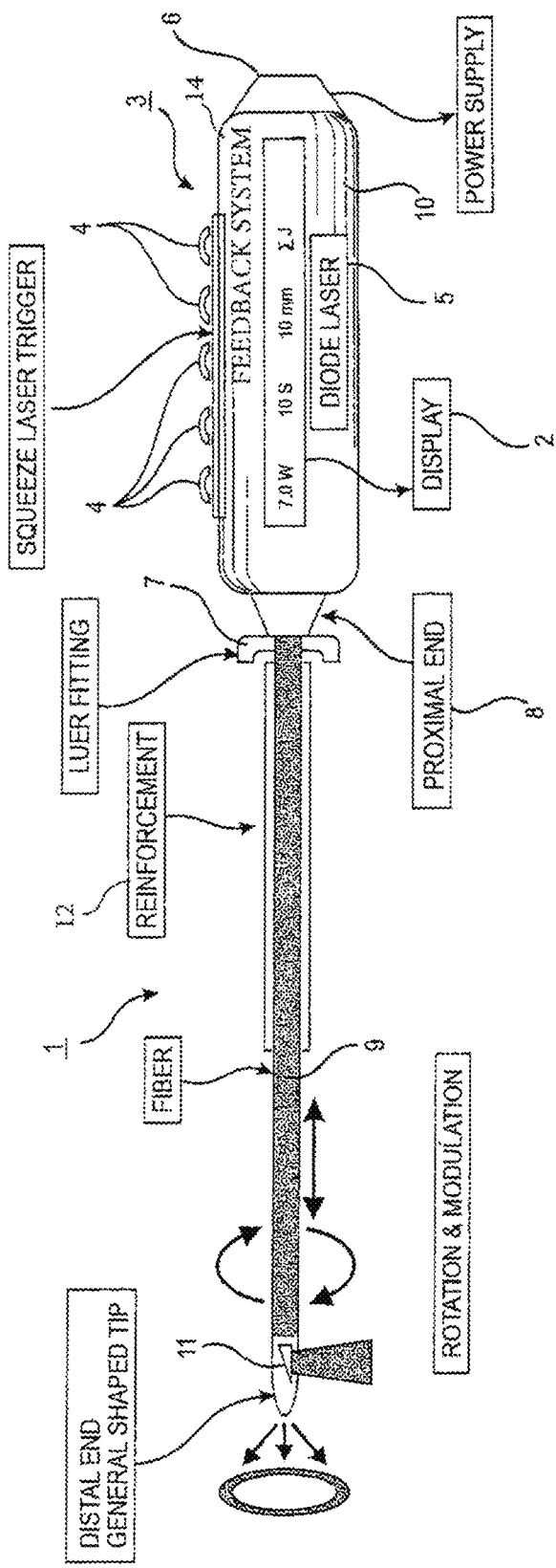

LASER SURGERY CONTROLLER WITH VARIABLE TIME DELAY AND FEEDBACK DETECTOR SENSITIVITY CONTROL

This application claims the benefit of U.S. Provisional Patent Application Ser. No. 61/316,569, filed Mar. 23, 2010, incorporated by reference herein.

BACKGROUND OF THE INVENTION

1. Field of the Invention

This invention relates to various improvements to the methods and apparatus disclosed in U.S. Patent Publication Nos. 2009/0062782 and 2009/0149845, and other similar laser treatment methods and apparatus involving monitoring of the treatment site for conditions such as overheating. The improvements include:

a. Addition of a variable time delay control to allow a surgeon to delay interruption of laser firing upon detection of overheating;
b. Addition of a detector sensitivity control for changing a sensitivity of the detector.

The invention may take the form of a hand held controller with an LCD or equivalent display and buttons or other inputs for setting the power output of the laser, the time delay, numerical aperture of the laser, and the sensitivity of the feedback detector.

The above listed improvements may be used separately or in any combination with each other or with any elements of the system disclosed in U.S. Patent Publication Nos. 2009/0062782 and 2009/0149845, or in combination with other surgical laser methods and systems, including those described in U.S. Patent Publication Nos. 2009/0062782 and 2009/0149845 as prior or related art. The methods and apparatus of the invention may be used with a variety of surgical laser procedures, including vascular surgery, liposuction, and applications involving gastroenterology, oncology, and urology.

2. Description of Related Art

A number of copending patent applications, prior patents, and prior publications, address the problem of detecting and preventing damage due to overheating of tissues and/or instruments/devices used to deliver laser energy to tissues during laser surgery or therapeutic laser procedures. For example, U.S. Patent Publication No. 2009/0062782 (based on U.S. patent application Ser. No. 12/047,819) discloses a safety feedback control unit in which radiation resulting from overheating at the location of the surgery is detected and used to control fiber position, laser activation, or rate of pullback. U.S. Patent Publication No. 2009/0149845 (based on U.S. patent application Ser. No. 12/073,922) discloses a radiation feedback system in which a sensor at the treatment end of the fiber monitors wavelengths indicative of temperature at the treatment end so that overheating of tissues can be detected before the flash of light from pyrolytic burning occurs, and monitoring of the output of the laser by downstream deflection, absorption, or fiber movement in response to overheating detection. In addition, various improvements on these safety or feedback systems are disclosed in PCT Publication PCT/US2009/006021. Each of these publications is incorporated herein by reference, and many the principles disclosed in U.S. Patent Publication Nos. 2009/0062782 and 2009/0149845, and PCT Publication No. PCT/US2009/006021, have been implemented in the LaserGuard™ system made by Optical Integrity, Inc. of Panama City, Fla.

The present invention is in response to various discoveries made by the inventor concerning the specific causes of damage and injury that occur during laser surgery. Conventionally, it was believed that damage caused by overheating during surgery was indicated by the pyrolytic glow that occurs during burning of tissues. As a result, various feedback systems were proposed to detect glowing of the tissues, and shut down of the laser upon detection of visible light from the glowing tissue. An example of such as system is disclosed in U.S. Pat. No. 5,098,427 (Hessel), owned by Messerschmitt-Bolkow-Blohm GmbH (MBB).

However, the inventor has discovered that glowing of tissues by itself does not necessarily indicate that damage or injury will occur. Instead, in many applications, the primary cause of fiber damage and resulting injury to the patient, namely fiber fusing or free electron absorption (FEA), normally occurs only when the fiber tip contacts the tissue during operation of the laser, which causes an increase in the temperature at the fiber tip. When the temperature at the fiber tip exceeds 1000 C, fiber fusing or FEA occurs, creating temperatures higher than 5000 C, at which point fiber fusing or FEA results in damage to the fiber.

There are several consequences of this discovery. First, it is not necessary to shut down the laser right away each time a glow is detected during surgery. Instead, it may be enough to simply move the tip of the laser away from the tissue and continue operating the laser, or to continue the procedure until the intensity of the glow or detected temperature exceeds a certain threshold. Second, the amount of energy that the laser can safely deliver to the patient without risk of injury may be higher than previously believed. These consequences suggest that certain laser procedures may be accomplished in a shorter time, without as many interruptions, thereby reducing discomfort to the patient. On the other hand, higher laser power can mean greater pain, and thus for certain applications, it might be desired to try and reduce the amount of laser energy delivered to the patient. The present invention seeks to take into account the inventor's discoveries concerning the specific causes of fiber damage and injury during laser surgery.

SUMMARY OF THE INVENTION

It is accordingly an objective of the invention to provide an improved surgical laser controller that takes into account the inventor's new discoveries concerning the causes of fiber damage and patient injury during laser surgery.

This objective is accomplished by providing an improved controller that increases control by the surgeon of the surgical procedure, and in particular that permits the surgeon or user to institute a variable time delay in the interruption of laser firing, and also to set the sensitivity of the detector, thereby improving the ability of the surgeon to avoid unnecessary interruptions during surgery and shorten the length of the surgery without sacrificing patient safety.

This objective is accomplished by providing a handheld controller that includes a display and user input to permit the user to set or change a time delay before firing of the laser is interrupted in response to feedback from an optical or temperature detector, and that furthermore permits the user to set the sensitivity of the detector. In addition, the handheld controller of the invention may include various features that enhance the ability of the user to manipulate the fiber tip in order to move the fiber away from a tissue before shut-down of the laser becomes necessary, including rotation and fiber position controls, laser modulation control, and a shaped fiber tip that enables precise control of laser output direction.

BRIEF DESCRIPTION OF THE DRAWINGS

The sole FIGURE is a side view of a handheld controller constructed in accordance with the principles of a preferred embodiment of the invention.

DETAILED DESCRIPTION OF THE PREFERRED EMBODIMENTS

As illustrated in the FIGURE, a handheld controller 1 includes a display 2, which may be in the form of an LCD or similar display capable of displaying such surgical parameters as laser power, a time delay between detection of overheating and interruption of the laser, a detector sensitivity or threshold temperature at which overheating is indicated, and a numerical aperture of the laser. In addition, the controller 1 includes a means for triggering the laser, such as a squeeze trigger 3, and buttons, dials, or other input means 4 for setting the time interval before laser interruption and detector sensitivity, as well as other parameters including, optionally, laser power output (which may also be controlled by the trigger). The controller also includes its own diode laser 5, a power connection at one end 6, and a fitting 7, such as a luer fitting, at a second end 8 for connecting the fiber 9 to the controller while permitting rotation of the fiber as well as movement of the fiber into and out of the main controller body 10. Optionally, the fiber may be surrounded by reinforcement 12, at least in the portion near to the controller body 10, and may have a shaped tip 11 to cause light to be emitted in a preferred direction from the tip of the fiber. The tip may have a variety of shapes, including inverted cone (recessed tip), orb, round, cone, beveled, and cap, to create a solid or angular output. In addition, a blue halo aiming beam (with other colors available), and a small numerical aperture and spot size, using 100 micrometer to 500 micrometer core fibers. The feedback system 14 included in the controller 1, may be any of the feedback systems disclosed in the above-cited publications or the LaserGuard™ system, or any other suitable feedback system.

In addition to providing the surgeon with improved control of interruptions during surgery, it may be possible to carry out the surgery at lower power, thereby possibly reducing pain felt by the patient. This can be accomplished by switching to silica clad fiber, which will not burn back, and by keeping the power density consistent. This feature of the invention is the result of the inventor's research into the thermal consequences of using plastic clad fibers. In particular, the inventor has found that, in applications where the fiber tip is buried in tissue, the plastic clad can quickly burn off, exposing the silica core allowing contamination on sides to steal energy. The inventor has measured the power drop off as much 50% within first few seconds of laser activation into tissue. Furthermore, if the fiber is buried in tissue and fiber tip with coatings burned back, there is a probability the tip could break off. When this occurs, the buffer, which now burns back but much slower, keeps temperature higher and readily imitates FEA. As a result, it may be preferred to switch back to a silca clad fiber which will not burn back and keep the power density consistent. As such, a given procedure could be performed at about half the power making the procedure safer and less painful for the patient. FEA could still occur, but at a much lower occurrence. Many surgical diode lasers put out as much 60-100 watts. But there are many cases where only 15 watts or less is required. Considering the concept of using silica clad may lower the power to less than 10 watts, albeit at a higher cost and with a lower numerical aperture than with plastic clad fibers.

Having thus described various preferred embodiments of the invention in sufficient detail to enable those skilled in the art to make and use the invention, it will nevertheless be appreciated that numerous variations and modifications of the illustrated embodiment may be made without departing from the spirit of the invention. It is therefore intended that the invention not be limited by the above description or accompanying drawings, but that it be defined solely in accordance with the appended claims.

I claim:
1. A handheld controller for laser surgical applications, comprising:
   a handheld main unit including a laser;
   a fitting on said handheld main unit for connecting a fiber to said laser;
   a display;
   a feedback system for detecting overheating at a treatment site based on a parameter related to overheating and interrupting firing of said laser after a preset time interval following detection of said parameter;
   a trigger on said handheld main unit for triggering the laser to cause said firing of the laser; and
   a variable time delay control input on said handheld main unit to allow a surgeon to manually set said preset time interval, and thereby delay firing of said laser following detection of said parameter to provide time for a user of the controller to pull back a tip of the fiber to prevent damage to the fiber from fiber fusing or free election absorption without interrupting the firing of the laser.

2. A handheld controller as claimed in claim 1, wherein said fiber is rotatable relative to said controller.

3. A handheld controller as claimed in claim 1, wherein said fiber has a shaped tip.

4. A handheld controller as claimed in claim 1, wherein said fiber is a silica clad fiber.

5. A handheld controller as claimed in claim 1, further comprising a detector sensitivity control for changing a sensitivity of the overheating detection.

6. A handheld controller for laser surgical applications, comprising:
   a handheld main unit including a laser;
   a fitting for connecting a fiber to said laser;
   a display on said handheld main unit;
   a feedback system for detecting overheating at a treatment site based on a parameter related to overheating and interrupting firing of said laser after a preset time interval following detection of said parameter;
   a trigger on said handheld main unit for triggering the laser to cause said firing of the laser; and
   a detector sensitivity control input on said handheld main unit for enabling a surgeon to manually set a sensitivity of the overheating detection in order to delay the interruption in firing of the laser and provide time for a user of the controller to pull back a tip of the fiber to prevent damage to the fiber from fiber fusing or free election absorption without interrupting the firing of the laser.

7. A handheld controller as claimed in claim 6, wherein said fiber is rotatable relative to said controller.

8. A handheld controller as claimed in claim 6, wherein said fiber has a shaped tip.

9. A handheld controller as claimed in claim 6, wherein said fiber is a silica clad fiber.

* * * * *